US006529232B1

(12) United States Patent
Kraas et al.

(10) Patent No.: US 6,529,232 B1
(45) Date of Patent: Mar. 4, 2003

(54) MEDICAL ENDOSCOPE WITH A VIDEO CAMERA

(75) Inventors: Mathias Kraas, Haseldorf (DE); Timo Wenzel, Hamburg (DE)

(73) Assignee: Olympus Winter & Ibe GmbH, Hamburg (DE)

( * ) Notice: Subject to any disclaimer, the term of this patent is extended or adjusted under 35 U.S.C. 154(b) by 0 days.

(21) Appl. No.: 09/527,557

(22) Filed: Mar. 16, 2000

(30) Foreign Application Priority Data

Mar. 20, 1999 (DE) .......................... 199 12 657

(51) Int. Cl.⁷ ................................. H04N 7/18
(52) U.S. Cl. ......................... 348/65; 600/109
(58) Field of Search ................. 600/109–110, 121–122; 348/65–76, 61; 385/117

(56) References Cited

U.S. PATENT DOCUMENTS 5,188,094 A * 2/1993 Adair .......................... 600/122
5,842,972 A * 12/1998 Wulfsberg ................... 600/167

* cited by examiner

*Primary Examiner*—Vu Le
(74) *Attorney, Agent, or Firm*—Rankin, Hill, Porter & Clark LLP

(57) ABSTRACT

A medical endoscope with a video camera, a substantially tubular outer housing, which surrounds a substantially tubular inner metallic housing, and a light guiding fiber bundle. The inner housing surrounding a rod lens image guide disposed distally of the camera in a vapor-tight manner. The camera is disposed within the inner housing.

2 Claims, 1 Drawing Sheet

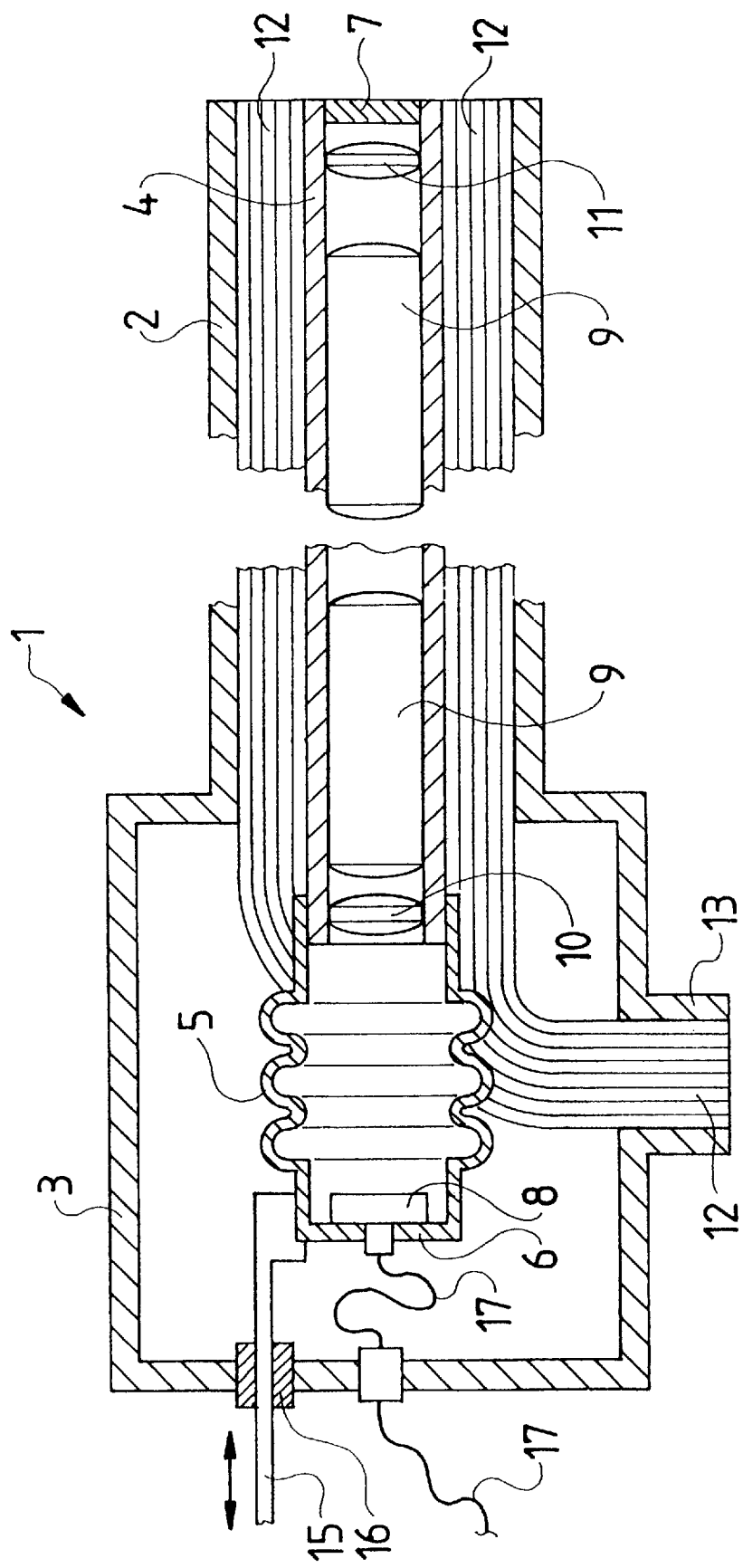

MEDICAL ENDOSCOPE WITH A VIDEO CAMERA

BACKGROUND OF THE INVENTION

Medical endoscopes are commonly used with a video camera. The video camera can be pushed onto the ocular of a conventional endoscope or incorporated into the endoscope. Endoscopes that incorporate a video camera are becoming increasingly widespread since operators want to work with a monitor, as opposed to the prior practice of working with an eye on the endoscope in an uncomfortable crouched position.

The absolute sterility of medical endoscopes before commencement of an operation has the highest priority. For instance, a very high degree of sterility is required with intra-arterial use. With the current state of the art the desired degree of sterility can only be achieved with hot steam sterilization in an autoclave. The endoscope is thus subjected to hot steam at high temperatures and pressures. The steam passes through the smallest links in the endoscope and condenses there on subsequent cooling. Drops of condensate and condensation are particularly disruptive on surfaces of lenses where they can critically impair the image quality.

Endoscopes of the type referred to above that have a rod lens image guide with a plurality of rod lenses and a large number of lens surfaces are particularly at risk to penetrating steam. In an endoscope of the type referred to above, the rod lens image guide is thus accommodated in a separate inner metallic housing with, for example, end windows soldered in a totally gas-tight manner in order to maintain the lens surfaces free of condensation, even with frequent autoclaving.

The outer housing surrounds the inner housing. A light guide fiber bundle, which is necessary for illuminating the field of view, is disposed next to the inner housing. Light guiding fibers are very difficult to seal since they are generally exposed at their ends with adhesive. The interior of the outer housing may, therefore, not be maintained free of condensation.

If a video camera is provided on such a device, either attached to the outer housing or incorporated in the outer housing, the entry window of the camera and the exit window of the rod lens optical system, which is disposed in the interior of the outer housing, also mist up.

SUMMARY OF THE INVENTION

It is the object of the present invention to construct an endoscope of the type referred to above with an optical path to the camera which is free of condensation.

In accordance with the invention, the camera is disposed within the inner housing. The camera is mounted in the inner housing in a completely vapor-sealed manner so that condensation can be reliably prevented.

The camera, which is arranged proximate to the rod lens image guide, must be disposed at a suitable focusing distance with respect to the rod lens image guide. The distance between the camera and the rod lens image guide should be adjustable, particularly in order to be able to compensate for subsequent changes of the spacing. Such spacing changes may result from tremors or thermal changes in the length of the inner housing. An adjustment device for changing the position of the camera within a vapor-tight housing, however, causes considerable sealing problems if, for example, sliding bushes or the like are used.

In further accordance with the present invention, the camera is secured to the proximal end member of a metal bellows, which constitutes a proximal end region of the inner housing. An adjustment device for changing the position of the camera engages the proximal end region of the bellows and moves the bellows relative to the distal portion of the inner housing accommodating the rod lens image guide. A focusing possibility or means for the camera is thus provided without an adjustment device having to pass through the vapor-tight inner housing.

BRIEF DESCRIPTION OF THE DRAWING

These and further features of the present invention will be apparent with reference to the following description and the drawing FIGURE, which is an axial sectional view of an endoscope in accordance with the present invention.

DETAILED DESCRIPTION OF THE PREFERRED EMBODIMENT

The drawing FIGURE shows a medical endoscope 1 with an outer housing comprising a shaft tube 2 and a main body housing 3 of larger diameter which is attached to the shaft tube 2 in a sealed manner. Provided within the outer housing 2, 3 is an inner housing comprising a system tube 4 with a metal bellows 5 attached to it in a sealed manner. Preferably, the metal bellows 5 is welded or soldered to the proximal end of the system tube 4. The proximal end of the metal bellows 5 is closed with a transverse plate 6. The distal end of the system tube 4 is closed with a transparent window 7. The transparent window 7 is preferably soldered in position in a conventional manner. The interior of the inner housing 4, 5 is thus sealed from the exterior in a completely gas-tight manner.

A video camera 8 is provided, which can comprise a complete camera with an electronic system and an optical system or only, as shown in the figure, an image sensor chip. The video camera 8 views the proximal end of a rod lens image guide, which is disposed in the system tube 4 and comprises a plurality of rod lenses 9, an ocular lens 10 and an objective lens 11.

The space between the shaft tube 2 and the system tube 4 is filled with light guiding fibers of a light guide fiber bundle 12. The bundle 12 terminates at the distal end in adhesive between the tubes 2 and 4. The proximal end of the light guide fiber bundle 12 is gripped in a socket 13. The socket 13 extends laterally away from the main body housing 3, and may be connected to a further light guide connecting cable (not shown) for connection to a light source.

In the construction illustrated in the figure, the camera 8 is disposed in the interior of the gas-tight inner housing 4, 5. Accordingly, the entire optical pathway (from the distal window 7 to the camera 8) is maintained free of steam and no surfaces can mist up and impair the optical quality.

The camera 8 must maintain a predetermined spacing from the proximal end of the rod lens image guide constituted by the rod lenses 9 and the lenses 10 and 11 so that the image is reproduced with optimum sharpness on the image sensor of the camera 8. Precise adjustment is necessary and subsequent adjustment can also be necessary if, for example, the length of the system tube 4, which comprises metal for reasons of absolute vapor-tightness, thermally alters.

For this purpose, an adjustment device is provided in the form of a push rod 15. The push rod 15 is mounted for sliding movement in the direction of the arrow. More specifically, the push rod 15 is mounted in a sliding guide 16 in the main body housing 3, as illustrated. The inner end of the push rod 15 engages the proximal end member of the metal bellows 5 and can move the bellows axially together with the camera 8 relative to the proximal end of the system tube 4. In other words, the camera is moved relative to the rod lens image guide disposed in the tube system 4, in order to set the correct focusing distance between the camera 8 and the rod lens image guide 9, 10, 11. The setting can be effected with means (not shown) that engage not only the end of the push rod 15 projecting out of the main body housing 3, but also the main body housing 3 itself. Such means can be constructed in the form of set screws or the like. The adjustment may thus be effected and the set position secured.

The camera 8 is connected to the exterior from the main body housing 3 with a connecting cable 17 that passes in a sealed manner through the transverse plate 6 of the bellows 5 and the main body housing 3. The free end of the cable 17 is connected to a suitable video device such as a monitor (not shown).

While the preferred embodiment of the present invention is shown and described herein, it is to be understood that the same is not so limited but shall cover and include any and all modifications thereof which fall within the purview of the invention.

What is claimed is:

1. A medical endoscope (1) comprising a video camera (8), a substantially tubular outer housing (2, 3), which surrounds a substantially tubular inner metallic housing (4, 5), and a light guiding fiber bundle (12), the inner housing (4, 5) surrounds a rod lens image guide (9, 10, 11) disposed distally of the camera (8) in a vapor-tight manner, wherein the camera (8) is disposed within the inner housing (4,5).

2. The medical endoscope as claimed in claim 1, wherein a proximal end region of the inner housing (4, 5) is formed as a metallic bellows (5) whose length may be altered in an axial direction of the rod lens image guide (9, 10, 11) and whose proximal end member (6) carries the camera (8), said bellows (5) being movable in the axial direction with respect to the outer housing (5) by means of an adjusting device (15).

\* \* \* \* \*